United States Patent [19]

Marx

[11] Patent Number: 4,573,992

[45] Date of Patent: Mar. 4, 1986

[54] APPARATUS FOR RECEIVING AND REINFUSING BLOOD

[75] Inventor: Günter H. Marx, Gauting, Fed. Rep. of Germany

[73] Assignee: Solco Basel AG, Birsfelden, Switzerland

[21] Appl. No.: 494,094

[22] Filed: May 12, 1983

[30] Foreign Application Priority Data

May 17, 1982 [DE] Fed. Rep. of Germany ....... 3218561

[51] Int. Cl.[4] .............................................. A61M 5/14
[52] U.S. Cl. ....................................... 604/408; 604/4; 604/141; 604/319; 128/DIG. 24
[58] Field of Search ................. 604/4, 27, 30, 35, 141, 604/146, 147, 319–321, 410, 408; 128/760, DIG. 24

[56] References Cited

U.S. PATENT DOCUMENTS

| | | |
|---|---|---|
| 2,886,035 | 5/1959 | Loutz . |
| 3,838,794 | 10/1974 | Cogley ............................ 604/141 X |
| 4,033,345 | 7/1977 | Sorenson et al. . |
| 4,047,526 | 9/1977 | Reynolds et al. . |
| 4,397,643 | 8/1983 | Rygiel ............................... 128/760 |
| 4,424,053 | 1/1984 | Kurtz et al. ............................ 604/4 |
| 4,432,763 | 2/1984 | Manshot et al. ................ 604/410 X |

FOREIGN PATENT DOCUMENTS

| | | |
|---|---|---|
| 196550 | 3/1958 | Austria . |
| 1803627 | 1/1960 | Fed. Rep. of Germany . |
| 461034 | 10/1968 | Switzerland . |

Primary Examiner—Stephen C. Pellegrino

[57] ABSTRACT

In apparatus for receiving and reinfusing a patient's own blood, a rigid container encloses a readily deformable inner container, blood being drawn into the readily deformable container by suction and being displaced therefrom by pressure applied between the outer container and the inner container, for pressure reinfusion. Alternatively, the apparatus has a concertina-like container which is held in its expanded condition by a support structure during the blood-intake suction phase, the blood being displaced from the container back into the patient by compression of the container. In another alternative form, the container is a concertina-like container with a high degree of resiliency adapted to expand it into an expanded condition, the container drawing blood from the patient by being compressed before being connected to the patient and then sucking the blood into the container by expansion under the effect of the resiliency.

8 Claims, 4 Drawing Figures

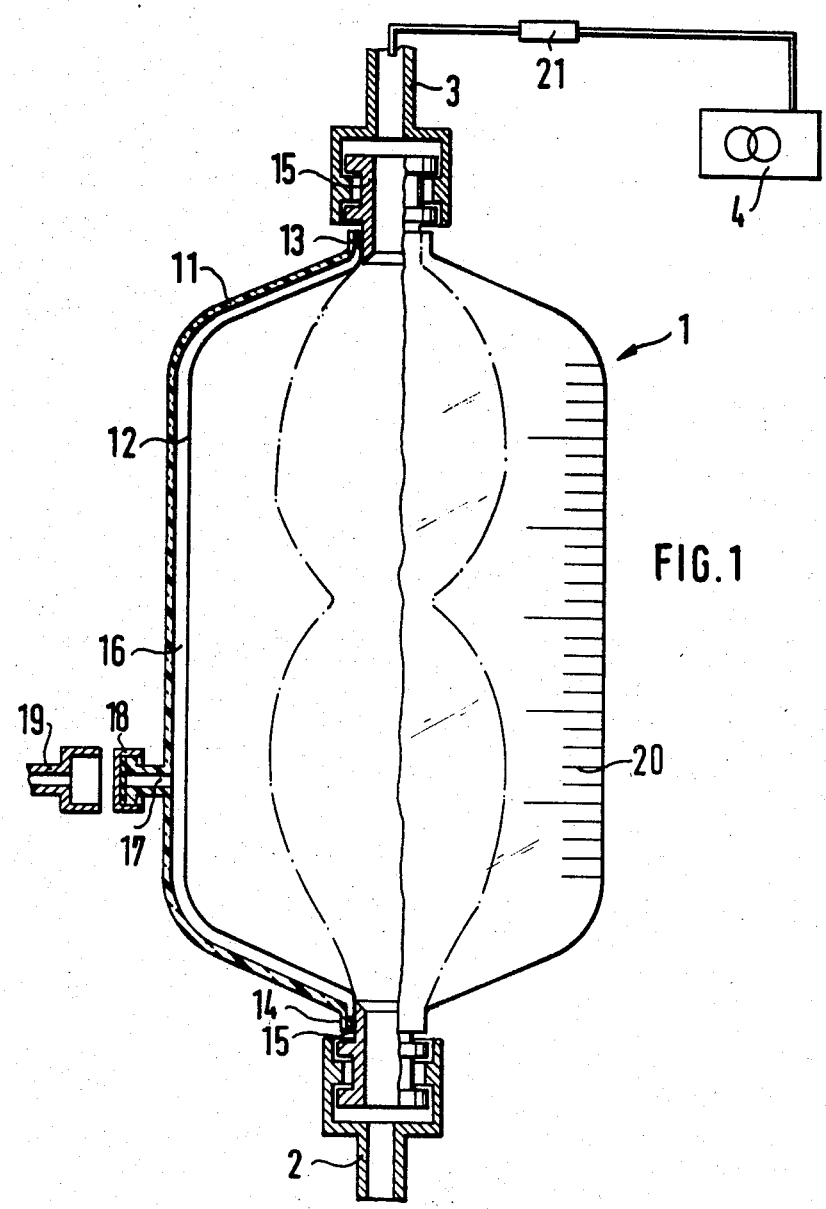

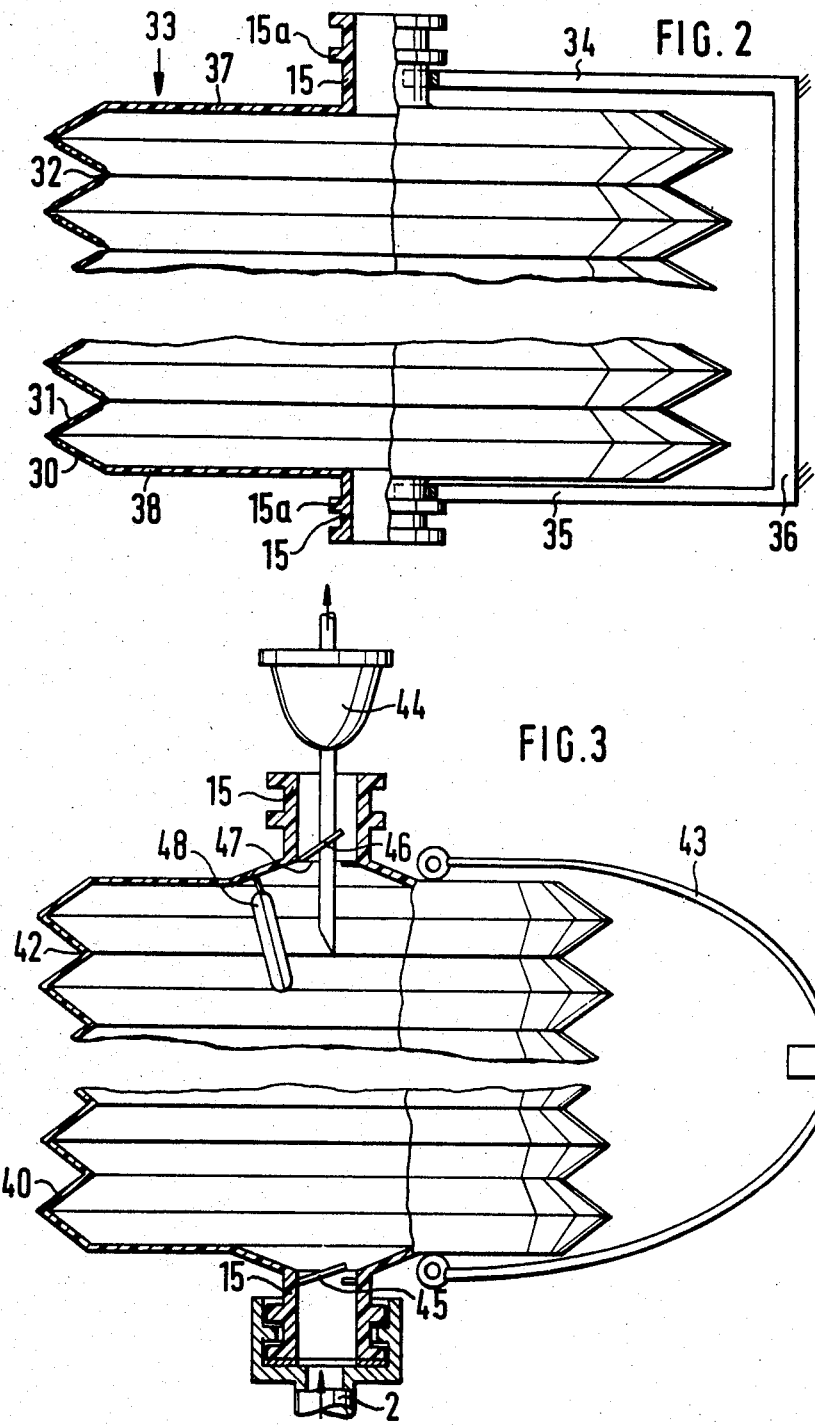

APPARATUS FOR RECEIVING AND REINFUSING BLOOD

BACKGROUND OF THE INVENTION

In certain surgical operations, for example and in particular in heart surgery, and also in the case of severe injuries or wounding, a patient may very often suffer from substantial blood losses which must be compensated by immediate blood transfusion if the life of the patient is not to be put at risk. Particularly in the case of surgical operations, the loss of blood is such that the blood which has been lost from the body is often still available, namely being in the form of accumulations of blood in cavities in the body of the patient, to which the surgeon has relatively ready access. It is therefore already known for the blood to be collected from such accumulations in the body, and reinfused into the same patient. Such a procedure which involves collecting the blood from and re-infusing the collected blood into the same patient is referred to as intra-operative autotransfusion.

Particularly in the case of heart surgery, for the purposes of performing autotransfusion, it is known for the patient to be connected to a heart lung machine for sucking the blood from the patient by means of pumps installed in the machine, and re-supplying the blood to the patient. However, such machines are extremely expensive and are therefore not available in every operating theatre, while in addition, in spite of the blood being carefully treated in machines of that type, the blood, being a fluid that is very sensitive and easily damaged, may nonetheless suffer a certain amount of damage, in its comparatively long path of flow through the machine from the patient and back to the patient again.

In an effort to remedy that problem, an apparatus has been put forward, for receiving and re-infusing a patient's own blood, wherein the blood is sucked in by way of a suction head, a suction line connected thereto and a suction connection, into a rigid container. The container communicates by way of at least one further connection with a vacuum source which is operative to produce, within the container, the reduced pressure required for sucking the blood from the patient. The container may have for example a capacity of about 2000 cm$^2$, and when the container is completely or substantially filled, the suction line is clamped off, the line connecting to the vacuum source is disconnected from the above-mentioned further vacuum connection and a conventional infusion fitment, possibly with a blood filter disposed on the upstream side thereof, is then fitted to the further connection from which the suction line was removed, so that the blood in the container can be infused back into the patient in the usual manner.

Although that arrangement has the advantage that the blood can be taken from the patient over a short flow path, thereby substantially avoiding damage to the blood, nonetheless it suffers from some disadvantages which mean that it is not entirely satisfactory. A major disadvantage is that that apparatus can only be used to re-infuse the blood from the container, into a blood vessel in the patient, in the manner of a conventional blood transfusion. As however an autotransfusion operation of the kind concerned herein is effected whenever a patient has suffered serious blood losses, it is also a point of major importance that the blood is re-infused back into the patient in the shortest possible time, as otherwise the patient may suffer from a considerable deficiency of body blood, such as to endanger the patient's life, over a considerable period of time. Such rapid re-infusion of blood can generally only be achieved by pressure infusion of the blood taken from the patient, but the above-described known apparatus is not designed to perform such pressure infusion and in addition, in consequence, such a pressure infusion cannot be effected without the danger of inducing an air embolism in the patient. Another disadvantage of the known apparatus is that, after an accumulation of blood in the patient's body has been drawn into the container, it is necessary to prevent air from being drawn into the container after the blood, which is effected by the suction line being closed off by means of a clamp; however, the suction force produced by the vacuum source still continues to apply a suction effect within the rigid container, and that may also give rise to the not inconsiderable danger of damaging the blood, as for example the reduced pressure or suction force may cause excessive expansion of the red blood corpuscles, and may even cause them to burst.

In another apparatus for intra-operative autotransfusion, which is similar to the apparatus just discussed above, the patient's blood is initially sucked into a rigid container and then re-infused into the patient from that container by means of a blood pump (see U.S. Pat. Nos. 4,047,526 and 4,033,345). In one embodiment of that known apparatus, the blood pump which is connected to the container is formed by an axially compressible concertina or harmonica-like arrangement which is releasably connected to the container and which can be operated to produce a vacuum which can overcome the vacuum in the rigid container. The harmonica-like arrangement is disconnected from the rigid container, after it is filled with blood, and handed over to the anaesthetist for the purposes of the re-infusion operation. In another form of the known apparatus, the blood pump is formed by a further container and is non-releasably connected to the rigid container in which the blood is received from the patient's body. The blood pump has a third inner, yieldably deformable container, and a respective check valve at its inlet and its outlet. The deformable container is compressed and re-expanded by alternately applying an increased pressure and a reduced pressure to a connection on the deformable container, so that in that way, and with the two check valves being suitably operative, the blood is sucked out of the first rigid container and then passed on to the patient through the outlet valve.

Although that apparatus permits the blood to be rapidly reinfused into the patient, it suffers from the disadvantage that the blood comes into contact with a comparatively large surface area which is foreign to the blood, namely the surfaces in the rigid container and in the blood pump, while in addition there is the danger for the blood to be detrimentally effected and possibly damaged by the vacuum produced in the blood pump, being a stronger vacuum than that in the rigid container.

SUMMARY OF THE INVENTION

An object of the present invention is to provide an autotransfusion apparatus which does not suffer from the disadvantages of the above-discussed prior art.

Another object of the present invention is to provide an autotransfusion apparatus which can take blood from a patient over a short flow distance and without damage, and also quickly reinfuse the blood over a short flow distance, again without damage.

Still another object of the present invention is to provide an autotransfusion apparatus which is simple and reliable in operation.

Yet another object of the present invention is to provide an autotransfusion apparatus which constitutes a fully independent and self-contained unit not requiring other vessels or containers for performing the reinfusion operation.

A further object of the present invention is to provide an autotransfusion apparatus which is operable to produce pressure infusion of the blood in order to restore the blood to the patient rapidly and without the risk of air embolism.

To achieve these and other objects, in a first aspect, the present invention provides an apparatus for receiving and reinfusing a patient's own blood, comprising a readily deformable container having a first connection for drawing blood from the patient by way of a suction line, and a further connection adapted to be connected to a reduced pressure or suction source, thereby to produce within the container the reduced pressure or suction force required to draw the blood from the patient. Disposed around the deformable container is a further rigid container which thus encloses the deformable inner container. The outside of the inner container and the inside of the outer container between them thus define a space to which there is connected a closable pressurising connection, for the selective feed of a pressure medium into the space between the inner and outer containers.

In the construction in accordance with the principles of the invention, as just set out above, blood is sucked in by way of the suction connection, by virtue of the reduced pressure or suction force obtaining in the outer or rigid container and within the readily deformable container. The reduced pressure in the container cannot result in collapse of the inner easily deformable container as, during the suction operation, the further space defined between the outside of the easily deformable, inner container and the inside wall of the rigid container is closed relative to the exterior, for example by a plug member or the like which is fitted to the pressure connection, or by the pressure connection being connected, during the suction operation, to a source producing a lower reduced pressure. When the container is suitably filled with blood, the suction line is clamped off or the suction connection itself is closed in a suitable manner, for example by means of a valve. A pressure source, for example a manually operable hand inflator of rubber ball type, is now connected to the pressure connection so that a pressure medium, in a controllable amount and under a controllable pressure, can then be introduced into the further space outside the inner or readily deformable container. As the rigid outer container does not experience any deformation under the pressure of the pressure medium introduced by the pressure source, the blood contained in the inner container is subjected to a pressure corresponding to the pressure of the pressure medium introduced; whereby, after the arrangement is connected to the patient by way of a pressure infusion fitment and possibly a blood filter connected to the upstream side thereof, the blood can be re-infused into the patient, in a short time.

It will be appreciated that the blood contained in the inner container is subjected to the pressure force from the exterior over a large area, more particularly, over the area of the outside of the readily deformable inner container, so that there is no serious danger of squeezing the red blood corpusles or otherwise damaging the constituents of the blood, which may frequently suffer damage of that kind when passing through pumps and by coming into contact with materials which are not entirely compatible with blood. It will also be appreciated that the inner container which accommodates the blood and which is preferably in the form of a bag or pouch, similarly to the conventional bags or pouches for blood transfusions, is made from a material which is compatible with blood, for example polyethylene, silicone rubber, PUR, PVC, and the like.

The bag or pouch which preferably constitutes the inner container is desirably of such a configuration that, in the undeformed condition, it substantially follows or matches the contour of the inside wall surface of the outer rigid container and is sealingly connected to the inside wall of the rigid outer container, preferably in the vicinity of the suction connection and the further connection thereon. The joint may be made by adhesive or by suitably welding the suitably selected plastic materials forming the outer and inner containers. In another advantageous feature of this form of the apparatus according to the principles of the present invention, which is of advantage from the manufacturing process point of view, the inner container is made for example from a suitable plastic film or foil, and connection nozzles or connecting means comprising a hard material are welded into the bag at the two ends thereof, the outside surface of the connecting nozzles or members forming respective sealing surfaces which are co-operable with corresponding sealing surfaces at apertures in the outer container, through which the connecting members therefore sealingly extend. That arrangement may be produced for example by sealing rings or the like being fitted into one of the respective pair of sealing surfaces in question. It is also possible however to use adhesive means or plastic welding at that location.

Instead of the inner container being in the form of a bag or pouch, it may alternatively be in the form of an axially compressible folding bellows or concertina-like container, with at least one of the two connections being formed thereon, by means of a connecting nozzle or like connecting member. If the connections are at the two ends of the axially compressible container, although it should be appreciated that that is not necessarily the case, one such connection must then be guided slidably and sealingly in a suitable aperture in the outer rigid container so that the blood contained in the inner container can be discharged therefrom by pressure medium introduced into the space defined between the inner container and the outer container, for reinfusion purposes.

In another aspect, the above-indicated objects of the present invention are achieved by an autotransfusion apparatus comprising a container having a suction connection for drawing blood from the patient and a further connection connectible to a suction source, for producing a reduced pressure in the container to draw blood thereinto. However, whereas in the above-discussed first aspect of the invention, the container is rendered rigid by virtue of suitable selection of the material and the wall thickness of the outer container, this second aspect of the present invention provides that the container for receiving the blood is an axially compressible concertina-like enclosure which is rendered axially rigid or non-deformable by a rigid mounting means or holder structure which is adapted to be secured to mutually oppositely disposed ends of the concertina-like container, to prevent collapse thereof under a reduced pressure in its interior. The concertina-like container comprises a material which is of suitable bending strength and the wall thickness thereof is so selected that, although the concertina-like container is axially compressible in the above-indicated manner, by virtue of for example a film hinge-type configuration at the bend edges where the individual fold portions of the concertina-like container are joined together, nonetheless the concertina-like container does not experience any deformation, or deformation to any substantial extent, in the radial direction, because of the stiffness and rigidity achieved by virtue of the concertina-like construction.

By virtue of a rigid holding or bracing means, for example a frame arrangement or a support structure, in which the concertina-like container may be fitted, when in the expanded condition, in such a way that the support structure secures positive connecting elements at the ends of the container, it is possible to provide that, when the reduced pressure is applied to the container, it still remains in its expanded condition, so that blood can then be sucked into the interior of the container by way of the appropriate suction connection thereon. When the container is then completely or substantially filled, the arrangement is closed off in a similar manner to that described above, to stop the further intake of blood. In this form of the apparatus according to the principles of the present invention however, the blood is reinfused into the patient not by connecting the apparatus to a pressure medium source, but by compressing the blood-containing enclosure in the axial direction. The compression operation to cause re-infusion of the blood may be carried out in various different ways, for example, manually, as by an anaesthetist, by putting it into a pressure arrangement, for example an inflatable pressure sleeve, or the like. Manual compression in particular has the advantage that it is then possible for the anaesthetist to more sensitively control the pressure, than can be achieved for example by using a feed of pressure air.

Having regard to the above-mentioned disadvantage of the known apparatus, whereby there is the danger of damage to the blood due to the reduced pressure within a rigid container continuing to act on the blood therein, although the suction line has been closed off as by means of a clamp, a development of the apparatus of the present invention, in the first-mentioned aspect and in the further aspect referred to above, provides that a pressure limiting means is disposed in the suction line connecting to the suction source, in order to limit the reduced pressure which can be produced in the blood-containing container. A simple form of such a pressure limiting means may comprise a portion of hose comprising silicone rubber, which is adapted to collapse at a given reduction in pressure therein. If the suction force reaches a pressure which is critical to the blood, the collapsible hose portion is compressed by the pressure difference between its interior and its exterior, thereby preventing further evacuation of the blood-containing container.

In a further aspect of the invention which is also based on the principle of the teaching of this invention of pressure reinfusion of the blood drawn from the patient, in a careful manner, the apparatus comprises a container for receiving blood drawn from the patient, in the form of an axially compressible concertina-like container which can be returned from a compressed condition to an extended condition by resilient means such as the inherent resiliency of the material constituting the container and/or by an external force which engages for example the ends of the container. Operatively associated with a suction connection for drawing blood from the patient is a check valve which is operable to open in such a direction as to permit a flow of blood into the container, while operatively associated with a further connection for reinfusion of blood from the container is a check valve which opens to permit a flow of blood out of the container.

In this further aspect of the invention, the suction effect is generated by expansion of the axially compressible container, from an initially compressed condition, such expansion being caused by inherent elasticity of the material constituting the container and/or a spring force. In order to ensure that the blood is not subjected to treatment likely to cause damage thereto, the degree of suction applied can be controlled by the extent to which the container is initially compressed.

In this construction also, the material and the wall thickness of the compressible container is so selected that the reduced pressure which occurs upon expansion of the container, in the interior of the container, does not result in the side walls of the container being deformed inwardly, as by the corrugated configuration of the container being inverted in an inward direction; that non-deformable effect can be readily achieved, by virtue of the higher degree of inherent stiffness of the corrugated-like configuration of the container. The check valves provided in the various connections of the container ensure that the blood which is sucked into the container cannot reverse its flow through the respective connection, and that the reduced pressure in the container, which is required for drawing the blood thereinto, is not destroyed by inflowing air from the connection which is subsequently to be used for the reinfusion operation. In the apparatus in accordance with this aspect of the present invention also, reinfusion can be effected by manually or mechanically compressing the container, in the same way as referred to hereinbefore.

The above-mentioned valve assembly in the container also enables a surgeon if necessary to re-compress the container by hand, when in an only partially filled condition, so that air also contained in the container is discharged through the check valve which is operative to open in an outward flow direction so that, by releasing the container again, further blood can be drawn into the container, to fill the part of the interior space therein from which the air was discharged by the fresh compression effect. In order in that situation to ensure that, when the container is compressed in order to discharge the air therein, blood is not also discharged from the container with the air, a preferred feature of this aspect of the invention provides that disposed upstream of the second check valve operatively associated with the further connection is a check valve operative to prevent a flow of liquid out of the container, the check valve being operative to check a flow therethrough only when that flow is constituted by a liquid. Such a liquid check valve may be for example a pivotal film or foil cushion which is arranged, upstream of said connection, within the compressible container, or alternatively a ball member which is heavier than air but lighter than liquid. When therefore the blood reaches the opening of the further connection, due to compression of the compressible container, the above-mentioned film or foil cushion or ball member, which up til then could not produce its flow-blocking action while the air was being discharged from the container by compression thereof, floats up on the blood as it moves towards the further connection, and causes that connection to be closed off. It would also be possible to use a hydrophobic filter means as the liquid check valve.

It will be appreciated that in all the basic aspects and embodiments of the apparatus in accordance with the principles of this invention, as set out above, the respective containers comprise materials which are acceptable and compatible from the physiological point of view, for example, polyethylene, polyurethane or polyamide, and are preferably also transparent or translucent to make it possible to monitor the level of blood in the container.

Further objects, features and advantages of the present invention will be apparent from the following description of preferred embodiments, given with reference to the accompanying drawings, and from the appended claims.

BRIEF DESCRIPTION OF THE DRAWINGS

FIG. 1 shows a view, partly in longitudinal section, of the container assembly of a first embodiment of the apparatus in accordance with the invention, wherein some components of the apparatus, being components which will be apparent to the man skilled in the art, are not illustrated in fully detailed form, for the sake of simplicity and clarity of the drawing, FIG. 2 shows a diagrammatic view in longitudinal section through the container arrangement in accordance with a second embodiment of the apparatus according to the invention, and FIG. 3 shows a view in longitudinal section, similarly to FIGS. 1 and 2, of the container arrangement of a third embodiment of the apparatus according to this invention.

DESCRIPTION OF PREFERRED EMBODIMENTS

Figure 1A:
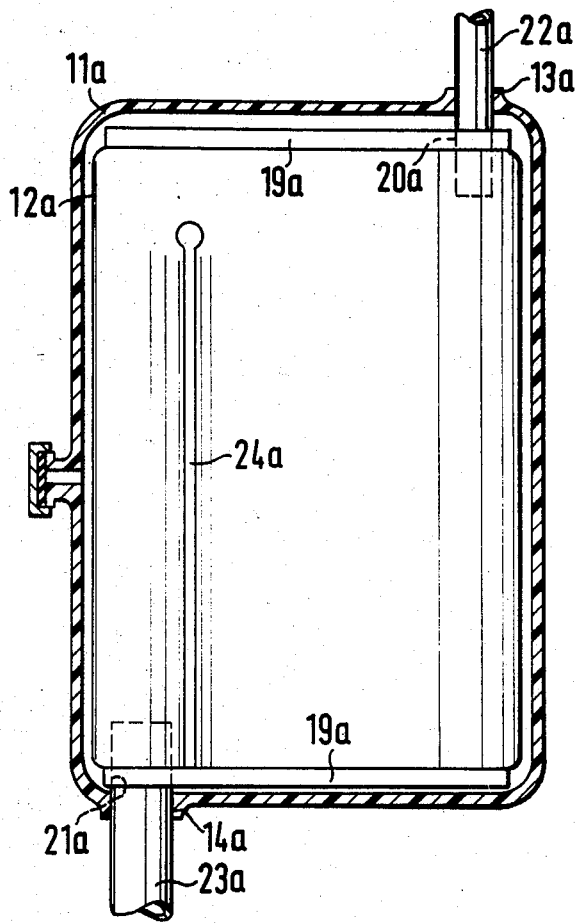
FIG. 1a shows a view in longitudinal section, similar to that shown in FIG. 1, of a modified form of the first embodiment of the apparatus.

Reference will now be made to the accompanying drawings showing various components and features of the apparatus according to the present invention, as will now be described.

The embodiment of the apparatus of which the major part is shown in FIG. 1, for receiving and reinfusing blood, comprises a container arrangement which is generally denoted by reference numeral 1. Connected to the container arrangement 1 is a suction line or conduit 2 which can be closed off by any suitable means, such as a clamp, and which in turn can be connected to a suction head for sucking blood into the apparatus. The container arrangement 1 is also connected to a releasable vacuum or reduced pressure or suction line or conduit 3, for connection to a reduced pressure or suction source, for example a vacuum pump, as diagrammatically indicated at 4. It should be noted at this point that the apparatus can also be connected to a per se known infusion fitment or instrument, possibly with a blood filter disposed upstream thereof, which can be connected to the container arrangement 1 in place of the line 2 or the line 3, and which serves for reinfusion of blood contained in the container arrangement 1, as will be described hereinafter.

As will be readily apparent from FIG. 1, the container arrangement 1 comprises an outer container 11 which is of a rigid form by virtue for example of the material used and the wall thickness employed, and an inner, readily deformable container 12 which is disposed within the outer container 11 and which may be for example in the form of a bag or pouch of any suitable material. The outer rigid container 11, which may be of any desired configuration but which is desirably substantially cylindrical, and which is substantially closed at its respective ends, as clearly shown in FIG. 1, is provided with apertures 13 and 14 at its two opposite ends. As shown in FIG. 1, each of the apertures 13 and 14 is surrounded by a collar portion which extends generally outwardly in the axial or longitudinal direction of the container 11, to form a kind of neck configuration. The purpose of the neck configurations at apertures 13 and 14 will become apparent below.

At its opposite ends, the bag or pouch 12 also has openings into which are fitted connecting members or nozzles as indicated at 15, being secured to the bag or pouch 12 for example by a welding operation. The connecting members 15 comprise a comparatively rigid plastic material to which the suction line 2 and the reduced pressure line 3 can be connected by means of suitable hose coupling arrangements diagrammatically illustrated in FIG. 1. When the bag 12 is in the substantially undeformed condition shown in solid lines in FIG. 1, the bag 12 is of a shape which substantially corresponds to the inside contour of the outer container 11 so that, in that condition, a closed space 16 defined between the outside of the inner bag 12 and the inside wall surface of the outer container 11 is of comparatively small volume. The space 16 is closed relative to the exterior of the container arrangement 1 by virtue of the outside surface of the connecting members 15 being sealed to the inside surfaces of the neck portions around the apertures 13 and 14 in the outer container 11. That sealing effect is produced for example by welding, by adhesive means, or by seals which are fitted into the respective sealing surfaces, and the like. In that way, the space 16 between the inner container 12 and the outer container 11 is accessible only by way of a pressure connection indicated in diagrammatic form at 17, which is provided on the wall of the outer container 11. The pressure connection 17 can be closed off, when not in use, by a removable cover as indicated at 18, while, in use of the arrangement, a pressure line 19 which is connected to a pressure medium source (not illustrated in the drawing) can be connected to the pressure connection 17 after the cover 18 has been removed.

The outer container 11 has a scale 20 to permit the level of filling of blood in the container arrangement 1 to be read off.

The wall thickness and the material of the outer container 11 are such that the outer container 11 is capable of withstanding the pressure forces occurring, both from the outside and from the inside, without substantial deformation. On the other hand, the bag or pouch 12 comprises a thin and easily foldable or deformable plastic film or foil material, for example polyethylene.

The line 3 incorporates a hose portion 21 comprising an easily deformable material such as silicone rubber to act as a reduced pressure limiting means, in order to ensure therefore that the reduced pressure generated within the inner container 12 by the source 4 cannot fall below a given pressure at which damage to the blood in the container 12 might occur.

The mode of operation of the construction illustrated by way of example in FIG. 1 is as follows:

When, for example in the course of a surgical operation, blood accumulates in a cavity in the body of the patient being operated on, blood may be sucked therefrom by means of the present apparatus, by connecting the line 3 to the reduced pressure source 4 while the suction line 2, with the suction head thereon, is introduced by the surgeon or an assistant into the accumulation of blood which is to be sucked away from the patient. As a result of the reduced pressure generated within the bag 12 by the source 4, blood is then sucked into the bag 12. As, at that time, the space 16 is sealed relative to the exterior by the cover 18 fitted on the pressure connection 17, or is alternatively also connected to the reduced pressure source 4 by way of a suitable line (not shown), the reduced pressure obtaining in the interior of the bag 12 cannot cause the bag 12 to fold or collapse inwardly. On the contrary, the bag 12 remains substantially in the condition shown in FIG. 1, as movement of the bag 12 inwardly away from the wall of the outer container 11, under the effect of the reduced pressure produced within the container 12, is opposed by the reduction in pressure in the space 16, which would occur when the wall of the bag 12 moves inwardly, so that the bag 12 is thus held in a condition of equilibrium, balanced between the pressure within the bag 12 and the pressure in the space 16. When the bag 12 and thus the container 11 is substantially filled, or when the accumulated blood in the patient has been sucked away into the apparatus, the suction line 2 is closed off by a suitable means such as a clamp (not shown), the reduced pressure line 3 is disconnected, and a pressure infusion fitment or instrument (not shown), possibly with a blood filter disposed upstream thereof in the usual way, is connectd to the connecting means 15 from which the line 3 has been disconnected. The needle of the pressure infusion instrument has already been inserted into one of the patient's blood vessels, and secured in place. The cover 18 is now removed from the pressure connection 17, or, where the pressure connection 17 has also been connected to the reduced pressure source 4, that connecting line is also disconnected from the pressure connection 17, and in its place, the pressure line 19 is connected to the connection 17. By a controlled feed of pressure medium, for example compressed gas, into the space 16, pressure can now be applied to the outside of the bag 12, within the container 11. That pressure accordingly acts on the blood contained in the bag 12 and feeds that blood to the patient by way of the connection arrangement 13, 15 and the pressure infusion instrument, the length of the period of time required for such pressure infusion depending on the amount of blood to be reinfused and also on the level of pressure applied in the space 16. FIG. 1 shows in broken lines the deformed condition of the bag 12 which will thus collapse inwardly as the blood is discharged from the bag 12 back into the patient, forming a folded configuration as that happens.

After the bag 12 has been emptied of all the blood contained therein, and is therefore in an at least substantially completely compressed condition, the bag 12 can be re-expanded to its original undeformed condition, by again connecting the connection 17 to a reduced pressure source, to draw the bag 12 outwardly into contact with the inside wall surface of the outer container 11.

Instead of using compressed gas as the pressure medium for producing the discharge of blood from the container arrangement 1, it is also possible to cause discharge of the blood contained in the bag 12, by means of an infusion solution which is supplied by means of a pump.

Reference will now be made to FIG. 1a showing a modified embodiment of an apparatus according to the principles of the present invention, wherein the outer rigid container 11a is of a circular cylindrical form and has apertures 13a and 14a at its oppositely disposed end walls, with the apertures being diametrically opposite to each other. In this embodiment, as in the embodiment described with reference to FIG. 1, the inner, readily deformable container may comprise a bag or pouch 12a which is formed from plastic film or foil material and which is of substantially square or rectangular configuration, being formed by welding together the ends of a portion of tubular film or foil. The weld seams are indicated at 19a.

The bag 12a has apertures 20a and 21a in the vicinity of the diagonally oppositely disposed corners of the bag 12a, for receiving tube or hose portions 22a and 23a respectively which preferably comprise the same material as the bag 12a and which are suitably secured in place, as by welding. The tube portion 22a leads to the reduced pressure source which is not illustrated in FIG. 1a but which is shown in FIG. 1, to which reference should therefore be made in this respect, while the tube portion 23a forms the suction connection for sucking in the blood, in a similar manner to the construction shown in FIG. 1. The bag 12a also has a weld seam 24a which originates adjacent the lower opening 21a and which extends parallel to the side edge of the bag, thus extending upwardly in FIG. 1a. The weld seam 24a joins together the opposite walls of the bag and extends to a position close to the upper edge of the bag, at the weld seam 19a. The positioning of the weld seam 24a thus forms a kind of channel or passage within the bag 12a, which extends in line with and therefore constitutes a prolongation of the tube portion 23a, into the interior of the bag 12a, so that blood which is sucked into the bag through the tube 23a is obliged first of all to rise up almost to the top of the bag, that is to say, to the top of the weld seam 24a, where it then flows over the upper end of the seam 24a in order to flow into the remaining, larger portion of the interior of the bag. That arrangement is intended to ensure that the blood which is sucked into the bag and which frequently contains air, thus constituting a blood-air mixture, is not sucked through the blood which is already contained in the bag 12a, by virtue of being obliged to flow first through the passage or channel defined by the weld seam 24a. If the inflowing blood were to be drawn through blood already contained in the bag 12a, the air contained in the inflowing blood would result in the continuous formation of foam in the blood in the bag, which could detrimentally affect and even damage the blood therein. It will be appreciated that this form of the bag 12a is very cheap to produce.

Reference will now be made to FIG. 2 showing a second form of the apparatus according to the principles of this invention, in which, instead of comprising the container arrangement 1 with the containers 11, 11a and 12, 12a, the illustrated apparatus comprises a container in the form of a concertina-like enclosure, as indicated generally at 30. The wall thickness and the material in the region of the folds 31 defined by the concertina-like container 30 are such that the folds are not compressed substantially in a radial direction, even when a reduced pressure obtains within the container 30. On the other hand, in the region of edges 32 at which the portions of the folds are joined together, the wall thickness of the container 30 is comparatively thin, to constitute a form of film hinge arrangement, so that the concertina-like container can be relatively easily compressed in an axial direction, as indicated by arrow 33.

At its oppositely disposed ends, the container 30 has connections 15 which can be connected to a suction line, and to a reduced pressure line and a pressure infusion instrument respectively, in the same manner as described above with reference to FIGS. 1 and 1a. The connections 15 have a rib at their free end, for suitably connecting the respective lines thereto, as shown in FIG. 1 for example, and also a further, outwardly projecting annular rib 15a, the purpose of which will now be explained.

As can be clearly seen in FIG. 2, the container 30 is engaged by a frame structure or holder means diagrammatically indicated at 36, which is of a generally U-shaped configuration providing respective arms 34 and 35, each of which has a generally forked end portion. In the expanded condition of the container 30, thus as shown in FIG. 2, the forked end of each of the arms 34 and 35 engages partially around a respective connection 15, under the annular rib 15a thereon, so as to hold the connections 15 at a spacing defined by the spacing between the forked ends of the arms 34 and 35 of the holder structure 36, thus also holding the container 30 in the expanded condition shown. It will be appreciated that the holder structure 36 and the co-operation thereof with the container 30 are such that the container 30 is held in the expanded condition, even when a reduced pressure is applied to the interior of the container 30, in a similar manner to the reduced pressure produced within the bag or pouch 12, 12a shown in FIGS. 1 and 1a respectively. It is possible for the two end walls 37 and 38 of the container 30 to be of a stronger or more rigid construction, or to be provided with a stiffening insert, in order to prevent the container 30 taking up an inwardly curved configuration at those points.

In the condition shown in FIG. 2, the container 30 forms the equivalent to the rigid outer container 11 in the construction shown for example in FIG. 1. It will be appreciated however that, as the container 30, as soon as it is removed from its position of form-locking engagement with the arms 34 and 35 of the holder structure 36, represents a readily deformable container corresponding to the bag or pouch 12 in the construction shown in FIG. 1, it also performs the function of that bag or pouch.

More specifically, the mode of operation of the construction shown in FIG. 2 is as follows:

First of all, a reduced pressure is produced in the interior of the concertina-like container 30, by connecting a reduced pressure source to one of the connections 15. Blood is sucked from an accumulation thereof in the body of the patient, into the interior of the container 30, by the reduced pressure therewithin, by way of the suction line connected to the connection 15. When the accumulated blood has been sucked away or when the container 30 has been entirely or substantially filled with blood, the suction line is closed off as by means of a clamp, and the reduced pressure line is disconnected and replaced by a pressure infusion arrangement, in the same way as described above with reference to FIG. 1. The container 30 can now be removed from the structure 36. The blood contained in the container 30 is then reinfused into the patient by axially compressing the container 30 in the direction indicated by the arrow 33. As already mentioned above, the container 30 may be axially compressed either manually or by introducing the container 30 into an inflatable pressure sleeve, or by means of another arrangement for applying pressure to the container 30.

Reference is now made to FIG. 3 showing another construction in accordance with the present invention, in which the container for receiving the blood to be reinfused is in the form of a concertina-like container 40 which in principle is the same as the container 30 shown in FIG. 2 but which has a higher degree of inherent elasticity than the container 30, by virtue of being of a suitable wall thickness, in the region of the edges 42 at which the fold portions defining the concertina-like configuration are interconnected. The inherent resiliency of the container 40 provides that, after the container 40 has been axially compressed, it will automatically return to its expanded condition. Such inherent resiliency can be assisted and promoted by a suitable spring means such as a spreading spring 43 which is connected to the end surface portions of the container 40 and which seeks to expand the container 40 in an axial direction. It would be possible to use such a spring means, instead of relying on the inherent resiliency of the container 40, as well as utilising both inherent resiliency and spring means.

Like the above-described embodiments, the container 40 also has connections 15. One of the connections 15 can also be coupled to a suction line 2, in the manner already described above, so that blood can be sucked into the interior of the container 40. However, in contrast to the previously described embodiments, the other connection 15, being the upper connection in FIG. 3, is not connected to a reduced pressure source, but instead is used exclusively in the operation of reinfusing the blood, for connecting a pressure infusion instrument of which FIG. 3 diagrammatically indicates the connecting pipe and the associated dome portion of a blood filter 44.

Disposed in the connection 15 to which the suction line 2 is to be connected is a non-return or check valve 45 which is operative to open in a direction such as to permit blood to flow into the container 40, while however being in a closed condition in the opposite direction, so that blood cannot be discharged from the container 40 through the lower connection 15 shown in FIG. 3. The opposite connection 15 which is subsequently connected to the pressure infusion instrument as shown in FIG. 3 also has a non-return or check valve 46 which is operative to open in a flow direction out of the interior of the container 40, while however producing its check function in the opposite direction of flow, namely, inwardly of the container 40. In addition, disposed in the vicinity of the opening 47 with which the check valve 46 is operatively associated and which leads to the connection 15 is a light air-filled film or foil cushion 48 which is so disposed that it hangs downwardly in the manner shown in FIG. 3, under the effect of its own weight. The cushion member 48 cannot be moved into a position in front of the opening 47, by virtue of a flow of air outwardly of the container through the check valve 46.

The mode of operation of the construction shown in FIG. 3 is as follows:

Firstly, the container 40 is axially compressed to its minimum volume by a manual pressure force, for which purpose it is necessary to overcome both the inherent resiliency of the concertina-like or corrugated wall of the container 30, and also the spring force of the spring 43, where such is provided. The suction line 2 is clamped off when the container 40 is in the compressed condition so that no air can pass into the container 40 and therefore the container 40 is retained automatically in the compressed condition. If now the suction head (not shown) connected to the suction line 2 is introduced into an accumulation of blood for example in the body of a patient, and the clamp closing off the suction line 2 is slowly released, the inherent elasticity of the container 40 and also the spring force applied by the spring 43 will cause the container 40 to expand in its axial direction. That causes an increase in the internal volume of the container 40, relative to its initial compressed condition, and blood will therefore be sucked into the container 40 through the suction line 2 and the check valve 45 which is thus in an open position. The other check valve 46, being closed, will prevent the entry of air into the container 40 during that phase of operation, so that the effect of reduced pressure in the container 40 is not nullified by an intake of air through the upper connection shown in FIG. 3. If, due to lack of attention or due to a certain amount of leakage, a certain quantity of air also passes into the container 40 so that the container is not completely filled with blood, although it has already expanded to the maximum extent, the surgeon or assistant may manually compress the container 40 again in order to remove that air from the container 40 by way of the connection 15 in which the check valve 46 is disposed. When that occurs, the cushion member 48 ensures that blood cannot additionally pass through the check valve 46, which would be undesirable. That is because the member 48 floats up on the surface of the blood in the container 40 and is thereby moved into a position in front of the opening 47 so as to close off the opening 47 and prevent blood from escaping from the connection 15 with the air which is being discharged therethrough.

When the container 40 is filled with blood in the manner just described above, it can be used for the reinfusion operation in the same manner as described above with reference to the embodiment shown in FIG. 2. In other words, the container 40 is manually or mechanically compressed to cause blood to be reinfused into the patient by way of the pressure infusion fitment 44 which is then connected to the connection 15. An important consideration in that connection is that the cushion member 48 is displaced from its position in front of the opening 47, by the connecting tube of the blood filter or by the corresponding tube of the pressure infusion fitment, so that the member 48 no longer closes off the opening 47 and blood can be discharged through the connection 15.

In a modified form of the embodiments illustrated, the connections 15 may be arranged on the same end of the container, in which case it is necessary to avoid short-circuits in regard to the flow of blood, by suitably extending the connecting structures into the interior of the container. It is also readily possible for the various valve functions, for example in respect of the check valves 45 and 46, to be performed at a different position, for example in the lines or conduits connected thereto, or short line or conduit portions which then themselves form the connections 15. It will be appreciated that the invention is also in no way restricted to the kind of connecting configurations illustrated in the specific embodiments shown herein. It should also be appreciated that, in the embodiment shown in FIG. 3, the inherent or natural resiliency of the container 40 can also be provided by springs or metal members which are embedded directly in or associated with the plastic material constituting the container 40.

It will be seen that all the embodiments described hereinbefore enjoy great ease of manufacture. There are many different forms of concertina-like or collapsible containers available on the market, and such containers can be readily adapted to the requirements of the present invention, by only slight modifications (for example, in regard to the connections). In the case of the construction shown in FIG. 1, the outer, rigid container 11 may be formed from two container halves which are joined together in an axial plane, with the bag 12 and its connecting members being inserted therein before the container halves are joined together.

As indicated above, the real purpose of the apparatus described herein is autotransfusion, that is to say, receiving and reinfusing a patient's own blood which is sucked for example from cavities in the patient's body or the like. Because a reduced pressure is constantly maintained within the container, by virtue of the reduced pressure source, for example as shown at 4 in FIG. 1, the apparatus is capable of sucking in blood, even after a blood-air mixture has been sucked in or when only air is sucked in by virtue of the suction head for drawing in the blood from the patient being inadequately immersed in the blood to be sucked in. However, it should be appreciatd that, by virtue of its design and construction, the apparatus can be used not only for autotransfusion, but can also be emloyed for drainage operations, for example for draining a wound, and can also be used in particular for blood donors.

With the embodiment according to FIG. 3 it may be thought about to combine the concertina-like container 40 integrally with a further container (not shown), so that the lower part of such combined container has a mere container function, while the upper part thereof has the combined function as container and as a pump. For this embodiment it is further advantageous to extend the lower connection 15 into the interior of the container, e.g. by means of a short tube, so that a sucked in mixture of blood and air is not directly drawn through the reservoir of blood already contained.

In order to avoid clamping of the suction line after accumulated blood has been sucked away, it is also possible to provide a check valve in that line.

Various other modifications and alterations may of course be made in the above-described embodiments and the modified forms thereof, without thereby departing from the spirit and scope of the present invention.

I claim:

1. An apparatus for receiving blood from a patient and reinfusing the blood into the patient, comprising: a deformable container, first connection means on the deformable container for connecting the deformable container to a suction line for aspirating blood from the patient, second connection means on the deformable container for connecting the deformable container to a reduced pressure source for sucking the blood into the deformable container from said suction line, one of said connection means also forming means for reinfusing blood from the deformable container into the patient, an outer container of substantial rigidity and having an inside surface defining with the outside of the deformable container a fluid-tight space, and third connection means on said outer container for selectively closing said space to prevent collapse of the deformable container during sucking of blood thereinto, and for connecting said space with a source of a fluid medium for increasing the pressure in said space for reinfusing the blood into the patient from said deformable container through said one connection means.

2. An apparatus as set forth in claim 1, wherein said deformable container is a bag which in an undeformed condition substantially follows the configuration of the inside surface of the outer container and which is sealingly connected to said inside surface.

3. An apparatus as set forth in claim 1, wherein said bag is sealingly connected to said inside surface of the outer container in the vicinity of said first and second connection means.

4. An apparatus as set forth in claim 2, wherein said bag has connection members comprising a hard material, constituting said first and second connection means, and wherein said outer container provides apertures through the wall thereof for receiving the respective connection members, said connection members being sealingly fitted in the respective ones of said apertures.

5. An apparatus as set forth in claim 1, wherein said deformable container comprises a flat bag of plastic film formed by first and second oppositely disposed wall portions having edges, the wall portions being connected together along said edges but leaving part of each thereof unconnected thereby defining an opening at each of two oppositely disposed edges of said bag, wherein said outer container provides apertures through the wall thereof, in operative association with respective ones of said openings, and wherein conduit means are secured in respective ones of said openings of said bag and are extended through respective ones of said apertures in said outer container, thereby to form said first connection means and said second connection means respectively.

6. An apparatus as set forth in claim 5, wherein said bag includes in its interior channelling means for guiding the inflow of blood into the bag in such a manner as to obviate said inflow passing through a substantial part of the blood already in the bag.

7. An apparatus as set forth in claim 6, wherein starting from the opening in the bag in which the conduit means constituting said first connection means is secured, the wall portions of the bag are joined together over a part of the bag towards the opposite said edge by a weld seam which extends towards the opposite said edge of the bag but which terminates short of the opposite said edge, thereby defining said channelling means.

8. An apparatus as set forth in claim 5, wherein said bag is of a substantially rectangular configuration and said openings are disposed diagonally opposite to each other.

* * * * *